United States Patent
Rokde et al.

(10) Patent No.: US 10,639,184 B2
(45) Date of Patent: May 5, 2020

(54) GASTRIC CALIBRATION TUBE

(71) Applicant: Covidien LP, Mansfield, MA (US)

(72) Inventors: Rajat R. Rokde, Maharashtra (IN); Mushtaque Syed Ahmed, Andhra Pradesh (IN); Jeetendra S. Bharadwaj, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 163 days.

(21) Appl. No.: 15/723,357

(22) Filed: Oct. 3, 2017

(65) Prior Publication Data
US 2018/0021159 A1 Jan. 25, 2018

Related U.S. Application Data

(62) Division of application No. 14/169,430, filed on Jan. 31, 2014, now Pat. No. 9,775,735.

(51) Int. Cl.
*A61F 5/00* (2006.01)

(52) U.S. Cl.
CPC .......... *A61F 5/0076* (2013.01); *A61F 5/0073* (2013.01); *A61F 5/0079* (2013.01); *A61F 5/003* (2013.01); *A61F 5/0036* (2013.01)

(58) Field of Classification Search
CPC .... A61F 5/0076; A61F 5/0073; A61F 5/0079; A61F 5/003; A61F 5/004; A61F 5/0089;
(Continued)

(56) References Cited

U.S. PATENT DOCUMENTS 4,114,625 A * 9/1978 Onat ............... A61M 25/10
                                               604/915
4,328,805 A    5/1982 Akopov et al.
(Continued)

FOREIGN PATENT DOCUMENTS

CA        2448961 A1    12/2002
CN      201365906 Y     12/2009
(Continued)

OTHER PUBLICATIONS

Australian Office Action issued in corresponding Australian Application No. 2014380149 dated Feb. 7, 2019, 3 pages.
(Continued)

*Primary Examiner* — Ariana Zimbouski
(74) *Attorney, Agent, or Firm* — Carter, DeLuca & Farrell LLP

(57) ABSTRACT

A gastric calibration tube includes a flexible elongate member, a pushing member, and a balloon member. The flexible elongate member has a proximal end portion, a distal end portion, and an outer surface that extends between the proximal and distal end portions. The outer surface defines a side opening. The flexible elongate member defines a lumen that is in communication with the side opening. The pushing member has a proximal portion and a distal portion. The distal portion is advanceable through the lumen of the flexible elongate member and out of the side opening of the flexible elongate member. The balloon member is secured to one or both of the flexible elongate member and the pushing member. The balloon member is inflatable to fix the gastric calibration tube within a patient's stomach.

11 Claims, 11 Drawing Sheets

(58) Field of Classification Search
CPC .... A61F 5/0036; A61F 5/0083; A61F 5/0069; A61B 2017/00827; A61B 2017/00818
See application file for complete search history.

(56) References Cited

U.S. PATENT DOCUMENTS

| | | | |
|---|---|---|---|
| 4,364,394 | A | 12/1982 | Wilkinson |
| 4,403,604 | A | 9/1983 | Wilkinson et al. |
| 4,774,949 | A | 10/1988 | Fogarty |
| 5,246,456 | A | 9/1993 | Wilkinson |
| 5,297,536 | A | 3/1994 | Wilk |
| 5,382,231 | A | 1/1995 | Shlain |
| 5,401,241 | A | 3/1995 | Delany |
| 5,458,131 | A | 10/1995 | Wilk |
| 5,462,528 | A | 10/1995 | Roewer |
| 5,465,709 | A | 11/1995 | Dickie et al. |
| 5,681,260 | A | 10/1997 | Ueda et al. |
| 5,718,666 | A | 2/1998 | Alarcon |
| 6,322,538 | B1 | 11/2001 | Elbert et al. |
| 6,558,400 | B2 | 5/2003 | Deem et al. |
| 7,153,131 | B2 | 12/2006 | Crohn |
| 7,713,281 | B2 | 5/2010 | Leeflang et al. |
| 7,744,613 | B2 | 6/2010 | Ewers et al. |
| 7,883,524 | B2 | 2/2011 | Chen |
| 8,016,851 | B2 | 9/2011 | Dillon et al. |
| 8,092,378 | B2 | 1/2012 | Roth et al. |
| 8,147,502 | B2 | 4/2012 | Albrecht et al. |
| 8,192,448 | B2 | 6/2012 | Bessler et al. |
| 8,216,271 | B2 | 7/2012 | Kassab et al. |
| 8,454,503 | B2 | 6/2013 | Roth et al. |
| 8,663,149 | B2 | 3/2014 | Gagner et al. |
| 9,775,735 | B2 | 10/2017 | Rokde et al. |
| 2002/0091395 | A1 | 7/2002 | Gabbay |
| 2004/0006351 | A1 | 1/2004 | Gannoe et al. |
| 2004/0092974 | A1 | 5/2004 | Gannoe et al. |
| 2005/0119674 | A1 | 6/2005 | Gingras |
| 2005/0159769 | A1 | 7/2005 | Alverdy |
| 2005/0203489 | A1 | 9/2005 | Saadat et al. |
| 2005/0251158 | A1* | 11/2005 | Saadat ............... A61B 17/1285 606/153 |
| 2006/0047298 | A1 | 3/2006 | Darzi et al. |
| 2006/0122462 | A1 | 6/2006 | Roth et al. |
| 2006/0200004 | A1 | 9/2006 | Wilk |
| 2006/0241344 | A1 | 10/2006 | Wilk |
| 2006/0241570 | A1 | 10/2006 | Wilk |
| 2007/0032702 | A1 | 2/2007 | Ortiz |
| 2007/0038239 | A1 | 2/2007 | Ritchie |
| 2007/0073098 | A1 | 3/2007 | Lenker et al. |
| 2007/0167960 | A1 | 7/2007 | Roth et al. |
| 2008/0132933 | A1 | 6/2008 | Gerber |
| 2008/0172079 | A1 | 7/2008 | Birk |
| 2008/0249404 | A1 | 10/2008 | Mikkaichi et al. |
| 2008/0249533 | A1 | 10/2008 | Godin |
| 2009/0093838 | A1 | 4/2009 | Paganon |
| 2009/0171382 | A1* | 7/2009 | Dillon ............... A61F 5/0036 606/192 |
| 2009/0198266 | A1 | 8/2009 | Cesare |
| 2009/0276055 | A1 | 11/2009 | Harris et al. |
| 2009/0287231 | A1 | 11/2009 | Brooks et al. |
| 2010/0121371 | A1 | 5/2010 | Brooks et al. |
| 2010/0179417 | A1 | 7/2010 | Russo |
| 2011/0178454 | A1 | 7/2011 | Gagner et al. |
| 2011/0213390 | A1 | 9/2011 | Kraemer et al. |
| 2011/0288576 | A1 | 11/2011 | Hoffman |
| 2012/0024292 | A1 | 2/2012 | Sandmore et al. |
| 2012/0123463 | A1 | 5/2012 | Jacobs |
| 2012/0165608 | A1 | 6/2012 | Banik et al. |
| 2012/0184981 | A1 | 7/2012 | Pecor et al. |
| 2012/0239061 | A1 | 9/2012 | Mathur |
| 2013/0165774 | A1* | 6/2013 | Nocca ............... A61F 5/0083 600/431 |
| 2014/0018722 | A1 | 1/2014 | Scott et al. |
| 2014/0114121 | A1 | 4/2014 | Trivedi |
| 2014/0371652 | A1 | 12/2014 | Aramaki et al. |
| 2015/0216698 | A1 | 8/2015 | Rokde et al. |

FOREIGN PATENT DOCUMENTS

| | | |
|---|---|---|
| CN | 102626536 A | 8/2012 |
| EP | 2172156 A1 | 4/2010 |
| EP | 2246013 A1 | 11/2010 |
| ES | 2326937 A1 | 10/2009 |
| JP | 2008161686 A | 7/2008 |
| JP | 2008532569 A | 8/2008 |
| JP | 3178309 U | 9/2012 |
| JP | 2013144164 A | 7/2013 |
| WO | 02096327 A2 | 12/2002 |
| WO | 2006076214 A2 | 7/2006 |
| WO | 2007110866 A2 | 10/2007 |
| WO | 2009097585 A1 | 8/2009 |
| WO | 2011042893 A1 | 4/2011 |
| WO | 2011161148 A1 | 12/2011 |
| WO | 2012138737 A1 | 10/2012 |
| WO | 2013123235 A1 | 8/2013 |
| WO | 2014062881 A1 | 4/2014 |

OTHER PUBLICATIONS

Extended European Search Report issued in European Application No. 14881081.5 dated Oct. 23, 2017.
Chinese Office Action issued in corresponding Chinese Application No. 2014800746072 dated Feb. 26, 2018.
Extended European Search Report dated Oct. 1, 2015, corresponding to European Application No. 15167342.3; 7 pages.
European Search Report dated Dec. 2, 2015, corresponding to European Application No. 15177233.2; 7 pages.
International Search Report and Written Opinion of hte International Searching Authoirity, dated Jul. 12, 2016, corresponding to International Application No. PCT/US2016/028046; 12 total pages.
European Search Report, dated Mar. 19, 2015, corresponding to European Application No. 14192226.0; 7 pages.
European Search Report, dated Mar. 24, 2015, corresponding to European Application No. 14192416.7; 7 pages.
Dietel et al., "Endoscopy of Vertical Banded Gastroplasty," The American Surgeon, May 1989, vol. 55; pp. 287-890.
Dietel et al., "Vertical Banded Gastroplasty: Results in 233 Patients," The Canadian Journal of Surgery, Sep. 1986, vol. 29, No. 5; pp. 322-324.
Mason et al., "Vertical Gastroplasty: Evolution of Vertical Banded Gastroplasty,"World Journal of Surgery, Sep. 1998, vol. 22, No. 9; pp. 919-924.
Extended European Search Report dated Sep. 17, 2015, corresponding to European Patent Application 15167339.9; 10 pages.
European Search Report dated Oct. 4, 2016, corresponding to European Application No. 16178267.7; 7 pages.
International Search Report issued in corresponding PCT/US2014/064752 dated Feb. 9, 2015.
Written Opinion issued in corresonding PCT/US2014/064752 dated Feb. 9, 2015.
International Preliminary Report issued in corresponding PCT/US2014/064752 dated Aug. 2, 2016.
Japanese Office Action issued in corresponding Japanese Application No. 2016-546796 dated Aug. 22, 2018.
Australian Examination Report issued in corresponding Australian Application No. 2014380149 dated May 24, 2019, 4 pages.

* cited by examiner

GASTRIC CALIBRATION TUBE

CROSS-REFERENCE TO RELATED APPLICATIONS

The present application is a Divisional Application which claims that benefit of and priority to U.S. patent application Ser. No. 14/169,430, filed on Jan. 31, 2014, (now U.S. Pat. No. 9,775,735) the entire content of which is incorporated herein by reference.

TECHNICAL FIELD

The present disclosure generally relates to surgical tools, and more particularly, to gastric calibration tubes used in bariatric procedures.

BACKGROUND

A gastric calibration tube is a surgical tool used to effectuate a surgical procedure on a patient's stomach in an effort to reduce excessive obesity in the patient. In use, the tube is advanced into a patient's body through an oral cavity and down through the esophagus into the stomach to provide delineation of the antrum of the stomach, irrigation/suction of fluids, and/or a sizing of a gastric pouch. While being advanced, due at least in part to the circuitous nature of this track, a clinician may need to reposition the tube in various orientations until the tube is properly aligned or bypasses any obstruction(s). Increasing maneuverability of the tube can reduce the time to perform a desired procedure.

SUMMARY

According to one aspect of the present disclosure, a gastric calibration tube includes a flexible elongate member, a pushing member, and a balloon member which provides ease of maneuverability and no procedural change from current procedures.

The flexible elongate member is dimensioned to extend between a patient's stomach and an oral cavity of the patient. The flexible elongate member has a proximal end portion, a distal end portion, and an outer surface that extends between the proximal and distal end portions. The outer surface defines a side opening. The flexible elongate member defines a lumen that is in communication with the side opening.

The flexible elongate member can include a reference indicator to enable a user to identify an orientation of the side opening. In some embodiments, the reference indicator is positioned proximally offset from the side opening. The reference indicator can be positioned in registration with the side opening.

The flexible elongate member defines a launch curve dimensioned to direct the pushing member through the side opening of the flexible elongate.

In certain embodiments, the distal end portion of the flexible elongate member is solid. The distal end portion of the flexible elongate member can define an aspiration lumen that extends distally to an opening defined in a distal end of the distal end portion.

The pushing member has a proximal portion and a distal portion. The distal portion is advanceable through the lumen of the flexible elongate member and out of the side opening of the flexible elongate member. The proximal portion of the pushing member is disposed within the lumen of the flexible elongate member as the distal portion of the pushing member is advanced out of the side opening of the flexible elongate member.

The balloon member is secured to at least one of the flexible elongate member and the pushing member. The balloon member is inflatable to fix the gastric calibration tube within a patient's stomach.

In some embodiments, the flexible elongate member defines a lumen in fluid communication with at least one of a fluid source and a vacuum source.

In certain embodiments, the flexible elongate member includes at least one depth marking.

According to another aspect, the elongate member defines a launch curve between the proximal end portion and the distal end portion. The proximal end portion and the launch curve can define a lumen in communication with a side opening defined in an outer surface of the proximal end portion. In some embodiments, the pushing member is positioned within the lumen of the elongate member and pushing member movable through the lumen and out of the side opening.

In certain embodiments, the pushing member curves as the pushing member slides along the launch curve and out of the side opening. Both the elongate member and pushing member can be formed of a flexible material.

According to yet another aspect, a method for advancing a gastric calibration tube includes advancing an elongate member through an oral cavity toward a stomach of a patient, selectively advancing a pushing member through the elongate member and out of a side opening defined in an outer surface of the elongate member to move the elongate member, and inflating a balloon supported on the elongate member in the stomach of the patient. The method can involve positioning the balloon within the antrum of the stomach. The method can include aspirating fluid within the stomach through the elongate member. The method can involve orienting the side opening of the elongate member with a reference indicator supported on the elongate member.

Other aspects, features, and advantages will be apparent from the description, the drawings, and the claims.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

As used herein, the term "clinician" refers to a doctor, nurse, or other care provider and may include support personnel. The terms "proximal" or "trailing" each refer to the portion of a structure closer to a clinician, and the terms "distal" or "leading" each refer to a portion of a structure farther from the clinician.

Figures 1A, 1B:
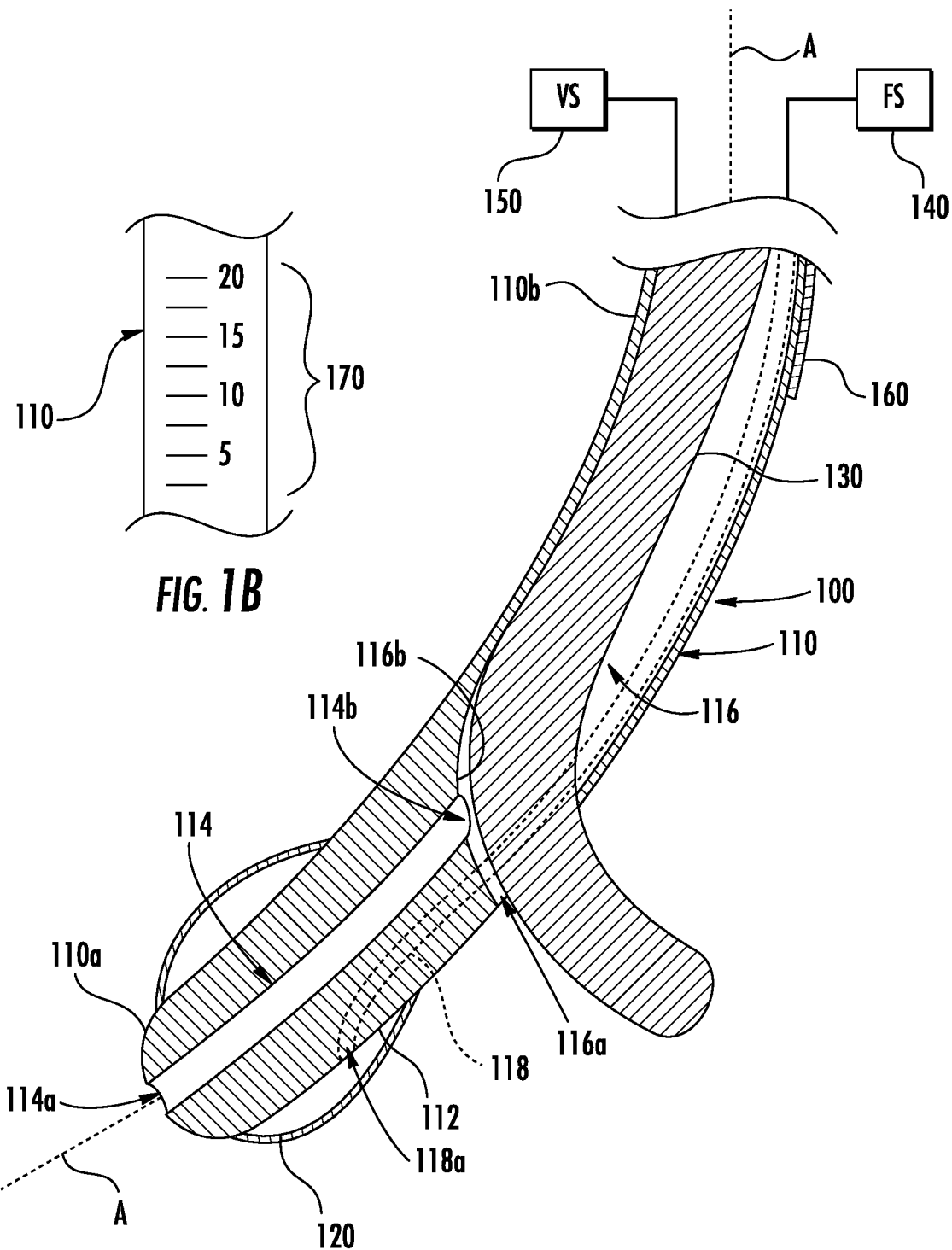
FIG. 1A is a side, cross-sectional view of a leading end portion of one illustrative embodiment of a gastric calibration tube shown coupled to a fluid source and a vacuum source in accordance with the principles of the present disclosure.
FIG. 1B is a side view of a portion of the gastric calibration tube of FIG. 1A.

Referring now to FIG. 1A, a gastric calibration tube 100 includes an elongate member 110, a balloon member 120 supported on the elongate member 110, and a pushing member 130 supported within the elongate member 110. It should be appreciated that, as used herein, the term balloon member refers to any structure defining a volume that is expandable upon introduction of fluid into the volume and, thus, can include a unitary arrangement of material and/or a multi-component arrangement secured together to form, for example, a bladder.

In use, as described in further detail below with reference to FIGS. 2-6, the gastric calibration tube 100 is insertable into an oral cavity (e.g., a mouth) of a patient and is advanceable distally (e.g., caudally) along a track that extends between an oral cavity and a stomach of the patient. If the gastric calibration tube 100 encounters an obstruction or otherwise become misaligned during advancement along the track, the pushing member 130 is adapted to advance out of the elongate member 110 and into engagement with a surface of a structure along the track (e.g., a wall of the esophagus) to drive the elongate member 110 away from the obstruction or back into alignment so that the elongate member 110 can be further advanced. When positioned in the stomach of the patient (e.g., the antrum or lower part of the stomach), the balloon 120 can be inflated to fix the gastric calibration tube 100 within the stomach and aid a clinician in performing a bariatric surgical procedure such as sleeve gastrectomy.

Referring again to FIG. 1A, the elongate member 110 can be formed of any material with sufficient flexibility to enable the elongate member 110 to maneuver along the patient's track between the oral cavity and the stomach. The elongate member 110 includes a leading end portion 110a and a trailing end portion 110b and defines a centerline "A" that extends between the leading and trailing end portions 110a, 110b.

The leading end portion 110a includes a distal tip 112. The distal tip 112 can be formed of any material that is solid or substantially solid. The distal tip 112 defines an aspiration lumen 114 that extends between a distal opening 114a defined in a leading end of the distal tip 112 and a proximal opening 114b defined in a trailing end of the distal tip 112. In some embodiments, as described in greater detail below, the aspiration lumen 114 extends along a length of the elongate member 110.

The elongate member 110 defines a lumen 116 that extends from the trailing end portion 110b to the trailing end of the distal tip 112. The lumen 116 is in fluid communication with a side opening 116a defined in an outer surface of the trailing end portion 110b. At least a portion of the lumen 116 (e.g., a leading end portion of the lumen 116) can be curved. A launch curve 116b is defined between a leading end of the trailing end portion 110b and a trailing end of the leading end portion 110a. More particularly, the launch curve 116b can be a curvature of the trailing end of the distal tip 112. As appreciated, the launch curve 116b can have any suitable geometry including any suitable radius of curvature. In some embodiments, the launch curve 116b defines a distal curvature of the lumen 116.

An inflation lumen 118 is defined in the elongate member 110 that is in fluid communication with an opening 118a defined in an outer surface of the distal tip 112. The balloon member 120 is supported on the outer surface of the distal tip 112 over the opening 118a. The balloon member 120 is adapted to receive inflation fluid (e.g., saline) through the inflation lumen 118 when the inflation lumen 118 is coupled to a fluid source 140 adapted to deliver the inflation fluid. Alternatively, and/or additionally, the inflation lumen 118 couples to a vacuum source 150 adapted to create a vacuum in the inflation lumen 118 to draw inflation fluid within the balloon member 120 out of the balloon member to deflate the balloon member 120. As appreciated, the fluid and/or vacuum sources 140, 150 enable a clinician to control the size of the balloon member 120 as desired.

The vacuum source 150 couples to the aspiration lumen 114 in the distal tip 112 to aspirate bodily fluids out of a surgical site such as the antrum of the stomach. As shown, the aspiration lumen 114 is in fluid communication with the lumen 116 so that aspirated bodily fluids will pass through the aspiration lumen 114 and the lumen 116. The side opening 116a functions as an inlet that draws bodily fluids in when the lumen 116 is coupled to a vacuum source 150. In some embodiments, the aspiration lumen 114 is defined along a length of the elongate member 110 and is separate from the lumen 116. In certain embodiments, the aspiration lumen 114 can extend from the distal end of the distal tip 112 (or any suitable location along the distal tip 112) to an exit location anywhere along the length of the trailing end portion 110b including a proximal end of the trailing end portion 110b.

A reference indicator 160 can be included on an outer surface of the elongate member 110 at a location on the elongate member 110 that enables a clinician to identify the location and/or orientation of the side opening 116a. More particularly, the reference indicator 160 functions as a reference to orient the elongate member 110 so that the pushing member 130 can advance along the launch curve 116b and out through the side opening 116a in any suitable direction as desired. It should be appreciated, that the pushing member 130 has an elongate body and can be formed of any suitable material with sufficient flexibility to enable the pushing member 130 to be directed by the launch curve 116b and out of the side opening 116a. In certain embodiments, as illustrated in FIG. 1B, the elongate member 110 includes one or more depth markings 170 on the outer surface of the elongate member 110 that function as an indicator for an insertion depth of the gastric calibration tube 100 along the track of the patient.

Figure 2:
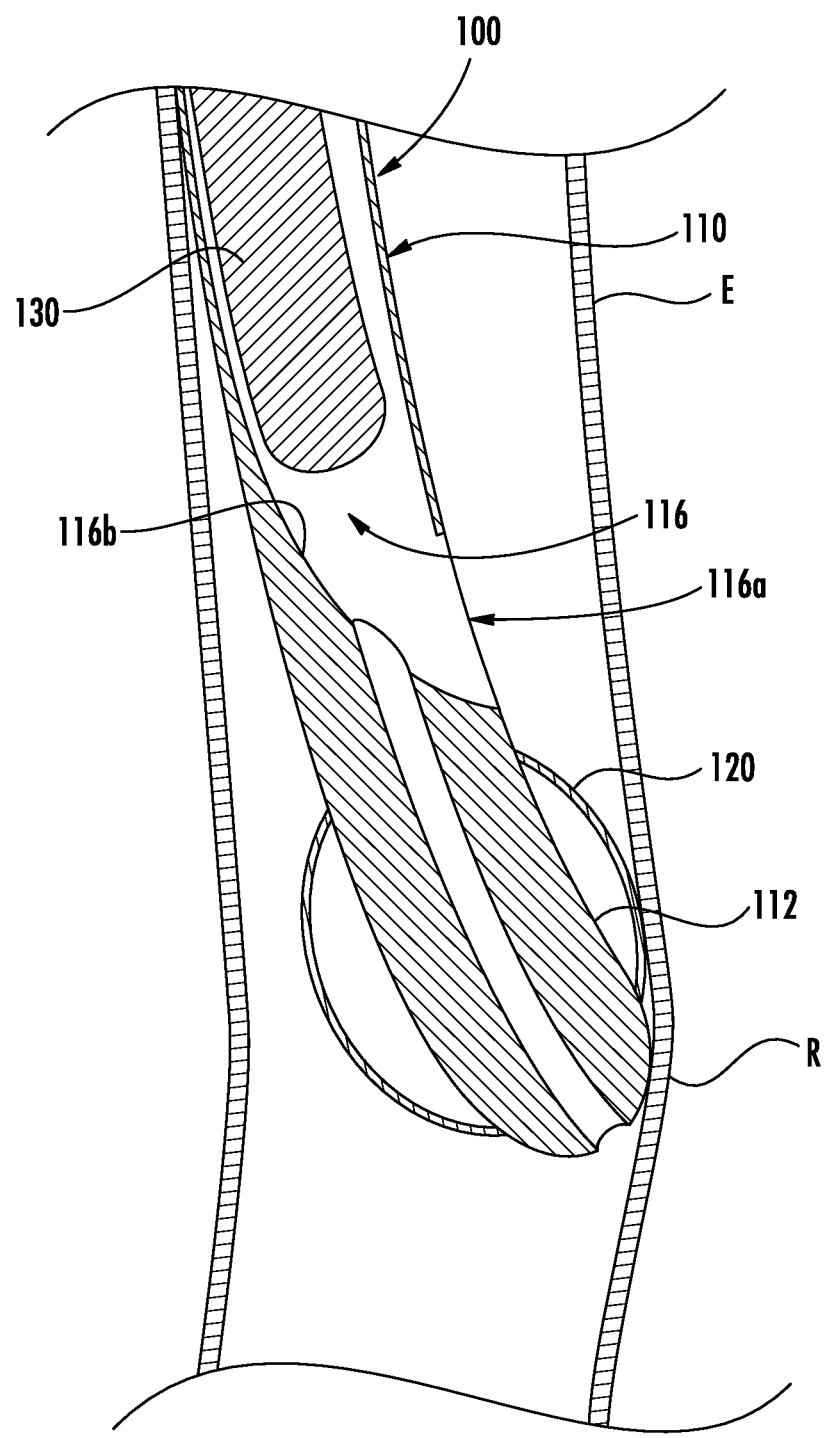
FIGS. 2 and 3 are progressive, side, cross-sectional views of the gastric calibration tube of FIG. 1A navigating through an esophagus.
Figure 3:
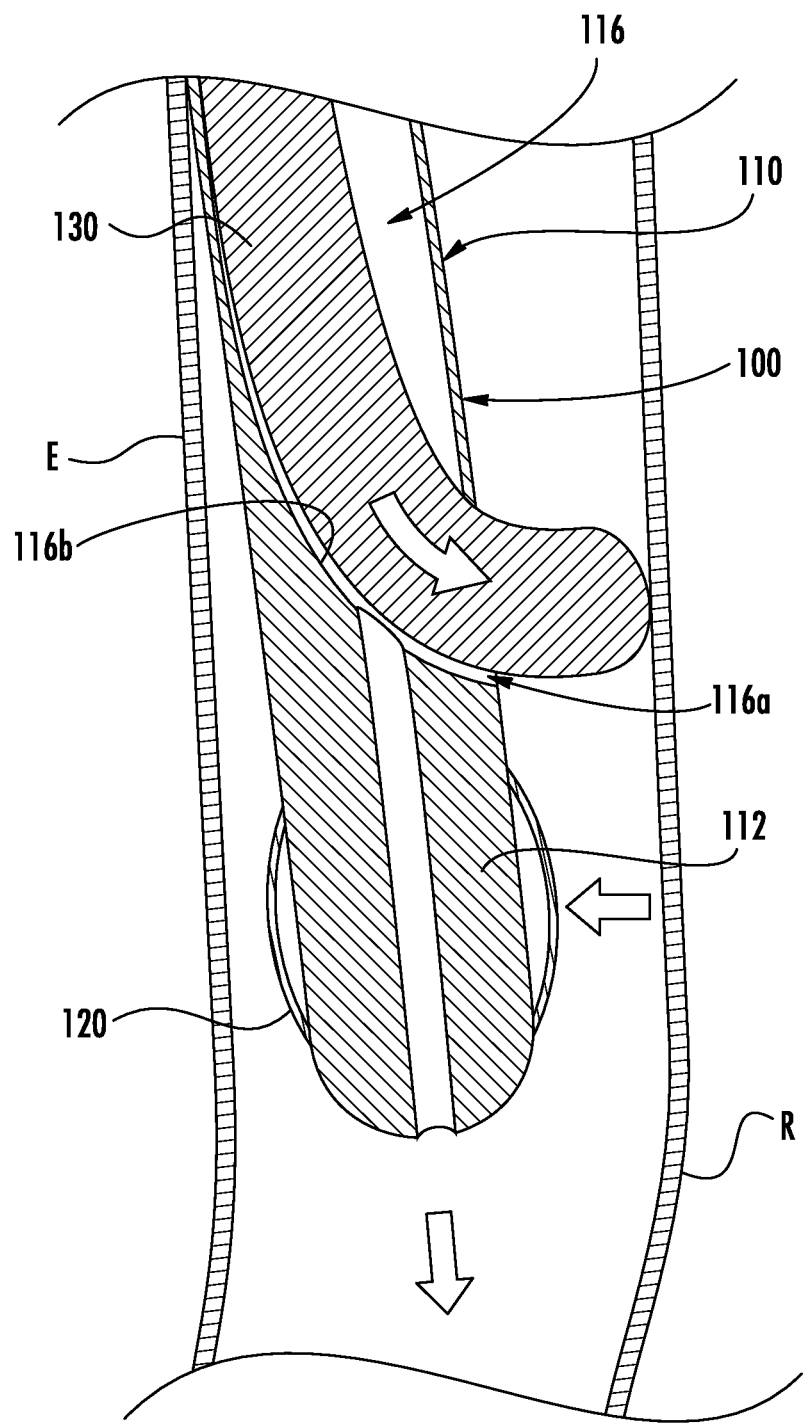

In an exemplary use, as illustrated in FIGS. 2-3, the gastric calibration tube 100 is insertable into a patient and is distally advanceable toward the stomach down a track that extends along the esophagus "E." Upon encountering an obstruction or becoming misaligned, for example, when the distal tip 112 of the gastric calibration tube 100 is frictionally restricted by curvature in the esophagus "E" at a point of restriction "R" that inhibits the gastric calibration tube 100 from distally advancing through the esophagus "E," the pushing member 130 can advance through lumen 116 into engagement with the launch curve 116*b*. As depicted in FIG. 3, the launch curve 116*b* directs the pushing member 130 out through the side opening 116*a* so that the pushing member 130 extends out from an outer surface of the elongate member 100 and into engagement with a surface such as an inner surface of the esophagus "E." An opposing reaction force, which results from the engagement between a distal end of the pushing member 130 and the surface of the esophagus "E," urges the elongate member 110 away from the obstruction or point of restriction "R." Upon moving the gastric calibration tube 100 away from the obstruction/point of restriction "R" and/or otherwise realigning the gastric calibration tube as desired, the pushing member 130 can be drawn back into the gastric calibration tube 100 and the gastric calibration tube 100 can be further distally advanced (e.g., past the obstruction and/or point of restriction "R").

Figures 4, 5:
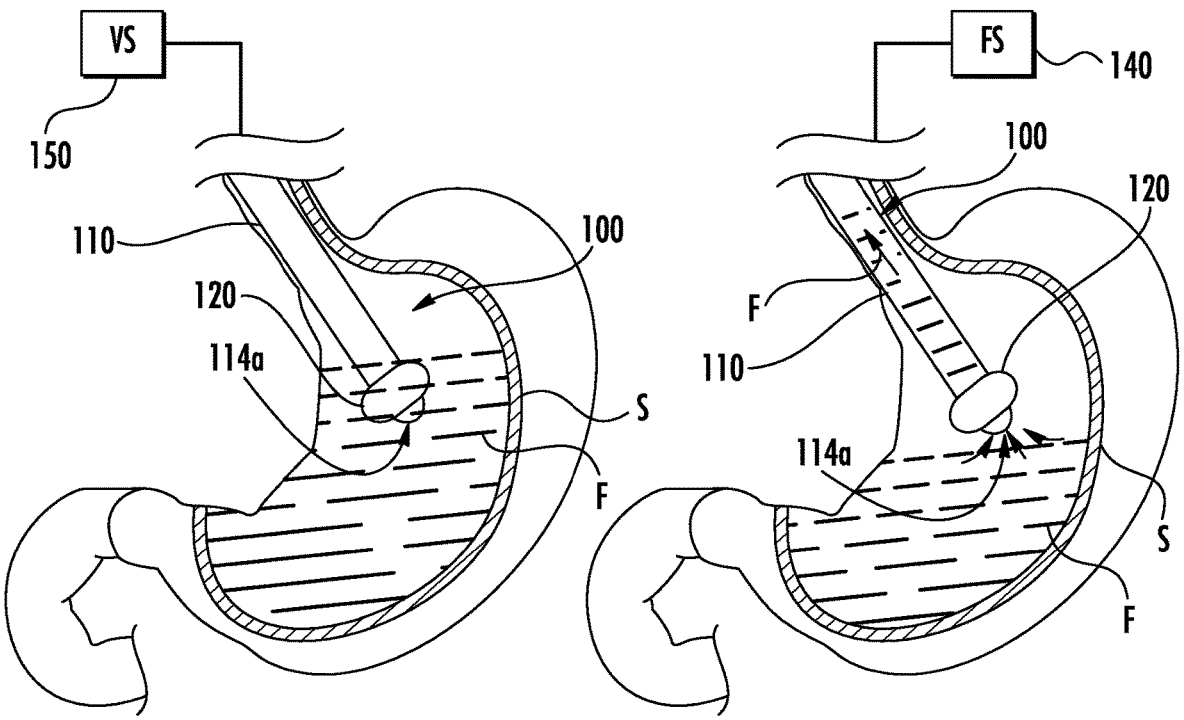
FIGS. 4 and 5 are progressive side views of the gastric calibration tube of FIG. 1A aspirating bodily fluid from within a stomach.
Figure 6:
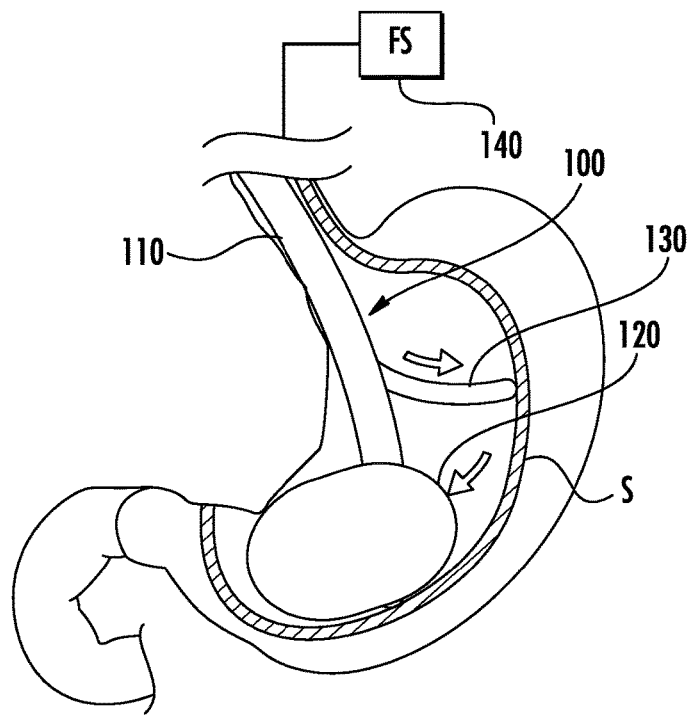
FIG. 6 is a side view of the gastric calibration tube of FIG. 1A shown secured to the stomach.

Referring to FIGS. 4-6, upon positioning the gastric calibration tube 100 into the stomach "S," the vacuum source 150 functions to aspirate bodily fluid "F" in the stomach "S." In particular, a vacuum created in the aspiration lumen 114 draws the bodily fluid "F" into the distal opening 114*a* of the distal tip 112 for proximal extraction of the bodily fluid "F" through the aspiration lumen 114 (see FIG. 5). As can be appreciated, the vacuum source 150 can also function to collapse the stomach or portions thereof to facilitate any suitable bariatric procedure such as sleeve gastrectomy.

As shown in FIG. 6, the pushing member 130 can be advanced out through the side opening 116*a* of the elongate member 110 so that launch curve 116*b* directs the pushing member 130 into engagement with an inner surface of the stomach "S" to urge the elongate member 110 toward any desirable location within the stomach "S" for inflating the balloon member 120 and/or for applying irrigation/aspiration within the stomach "S." For example, reaction force resulting from engagement of the pushing member 120 with the inner surface of the stomach "S" positions the elongate member 110 adjacent the antrum of the stomach "S" so that the balloon member 120 can be inflated within the antrum.

It should be appreciated that the inflation source 140 couples to the gastric calibration tube 100 to partially and/or wholly inflate the balloon 120 to fix the gastric calibration tube 100 within the stomach "S" (e.g., the antrum) and aid the clinician in performing the bariatric surgical procedure. For example, in a sleeve gastrectomy procedure, with the balloon 120 inflated in the antrum of the stomach, a clinician can remove a large portion of the stomach and staple the remaining portion together to limit the size of the patient's stomach for helping the patient lose weight.

Figure 7:
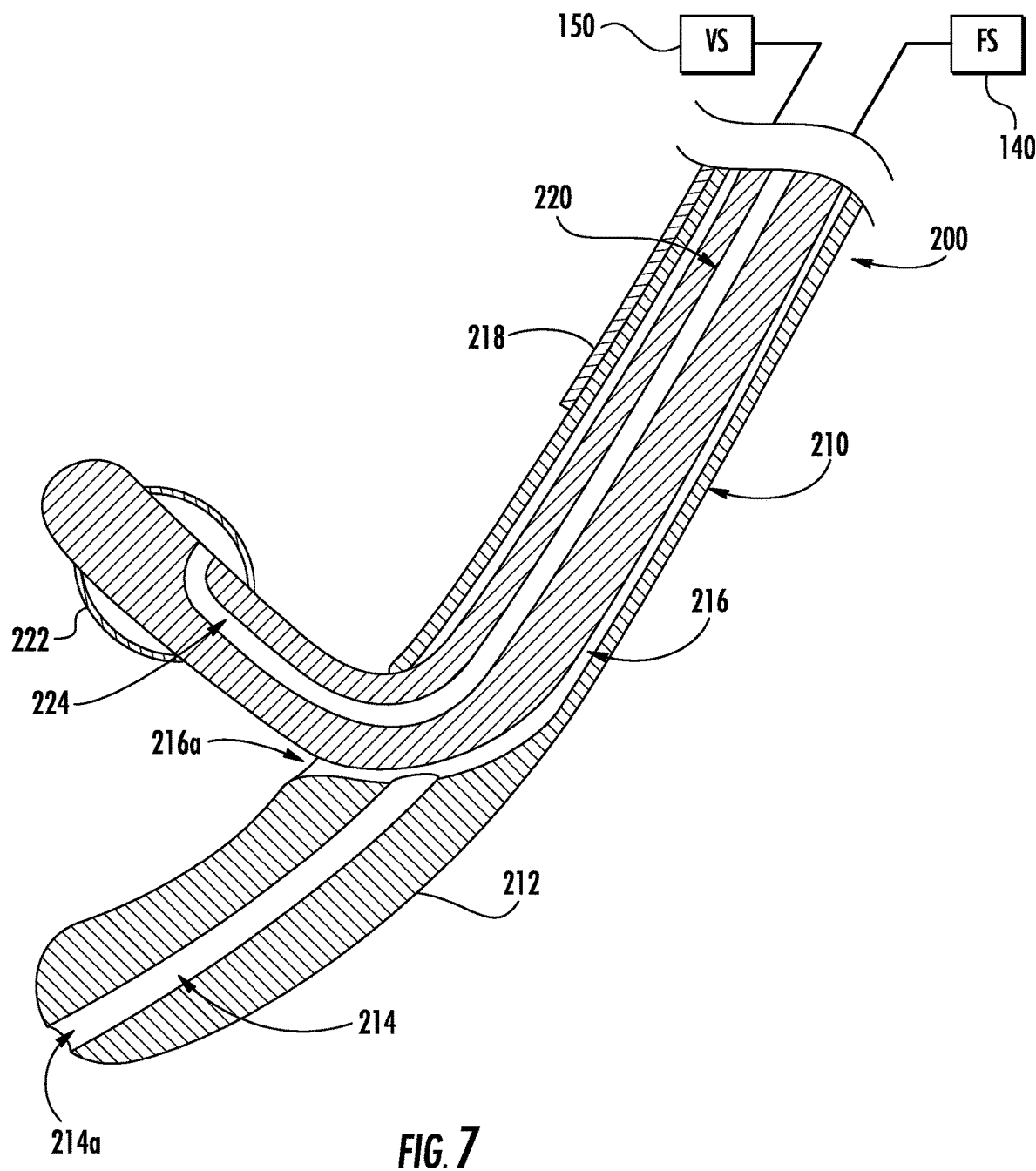
FIG. 7 is a side, cross-sectional view of a leading end portion of another illustrative embodiment of a gastric calibration tube shown coupled to a fluid source and a vacuum source in accordance with the principles of the present disclosure.

Referring now to FIG. 7, another embodiment of a gastric calibration tube, generally referred to as gastric calibration tube 200, is shown. Gastric calibration tube 200 is substantially similar to gastric calibration tube 100 and is only described herein to the extent necessary to describe the differences in construction and operation of the gastric calibration tube 200. In general, the gastric calibration tube 200 includes an elongate member 210, a pushing member 220, and operably couples to one or both of the fluid source 140 and the vacuum source 150.

The elongate member 210 includes a distal tip 212 and defines an aspiration lumen 214 and a lumen 216. The aspiration lumen 214 extends to a distal opening 214*a* defined in the distal tip 212. An outer surface of the elongate member 210 defines a side opening 216*a* that is in fluid communication with the lumen 216. In some embodiments, the elongate member 210 includes a reference indicator 218 that is positioned on the outer surface of the elongate member 210 in registration with the side opening 216*a*. Similar to reference indicator 160 of the gastric calibration tube 100, reference indicator 218 functions to identify the location and/or orientation of the side opening 216*a* to facilitate deployment accuracy of the pushing member 220 into a desired surgical site. Although not shown, the elongate member 210 can also include one or more depth markings similar to those shown in FIG. 1B.

The pushing member 220 has an elongate body that supports an inflatable balloon 222 on an outer surface of a distal end portion of the pushing member 220. The pushing member 220 defines an inflation lumen 224 in fluid communication with the inflatable balloon 222 to enable the balloon 222 to receive inflation fluid (e.g., saline) when the inflation lumen 224 is in fluid communication with the fluid source 140.

In an exemplary use of the gastric calibration tube 200, the pushing member 220 functions to enable the gastric calibration tube 200 to bypass an obstruction and/or point of restriction "R" as described above with respect to the pushing member 130 of the gastric calibration tube 100.

Figures 8, 9:
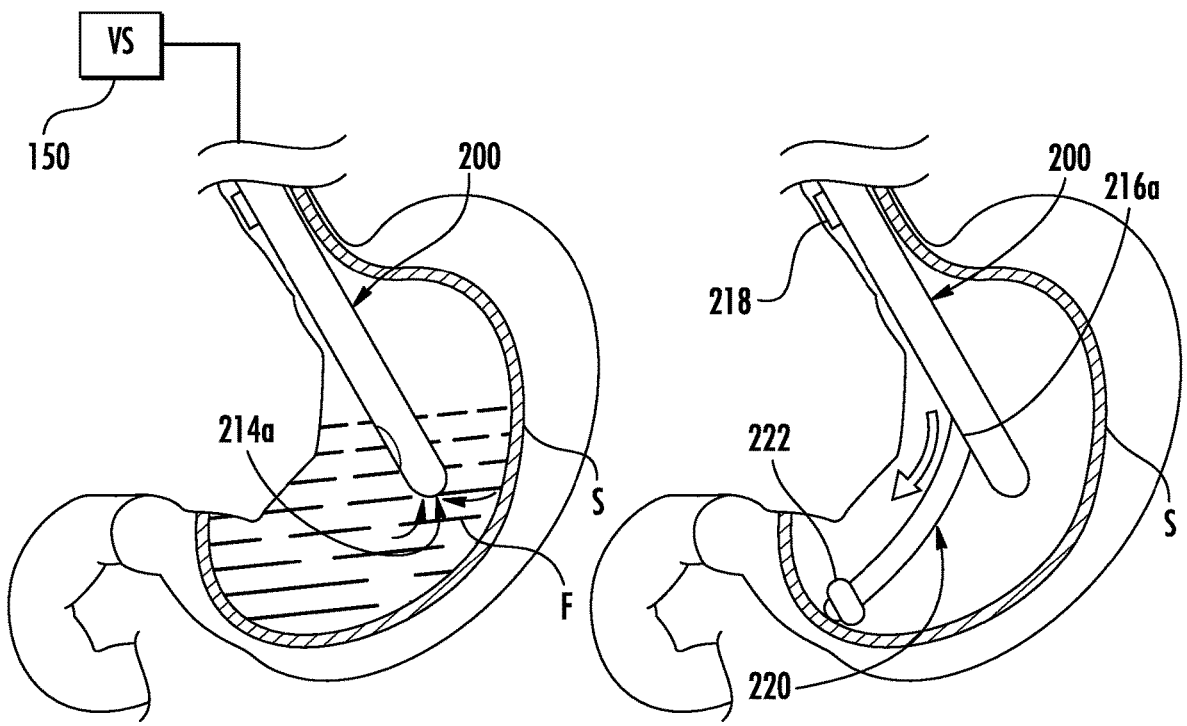
FIGS. 8-10 are progressive, side views of the gastric calibration tube embodiment of FIG. 7 which illustrate the tube aspirating bodily fluid from within a stomach and securement of the tube to a patient's stomach.

With reference to FIG. 8, when the gastric calibration tube 200 is positioned in the stomach "S," the vacuum source 150 can function to aspirate bodily fluid "F" from within the stomach "S" as described above with respect to gastric calibration tube 100. More particularly, the vacuum source 150 creates a vacuum in the aspiration lumen 214 and draws the bodily fluid "F" into the distal opening 214*a* for proximal extraction.

Figure 10:
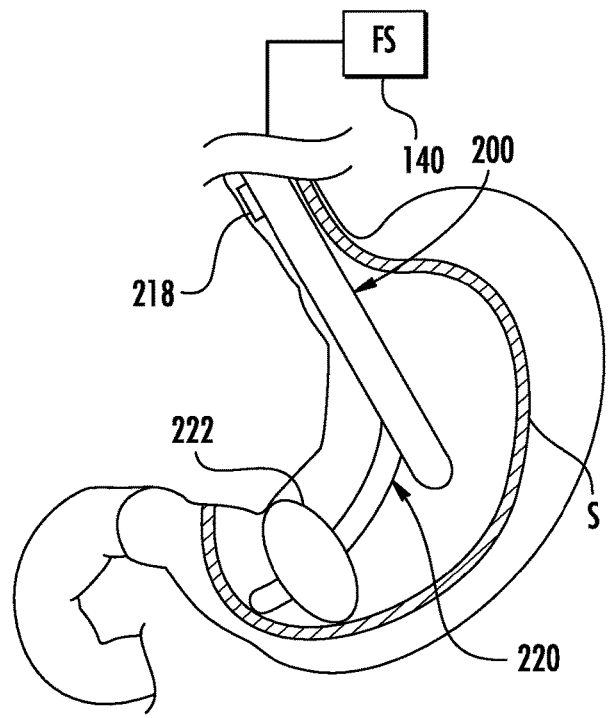

Referring also to FIGS. 9-10, the pushing member 220 can be advanced out of the side opening 216*a* and positioned at any suitable location in the stomach "S." As appreciated, when in fluid communication with the balloon 222 supported on the pushing member 220, the inflation source 140 can function to partially and/or wholly inflate the balloon 222 to fix the gastric calibration tube 200 within the stomach "S" as necessary to aid the clinician in performing a bariatric surgical procedure.

Figure 11:
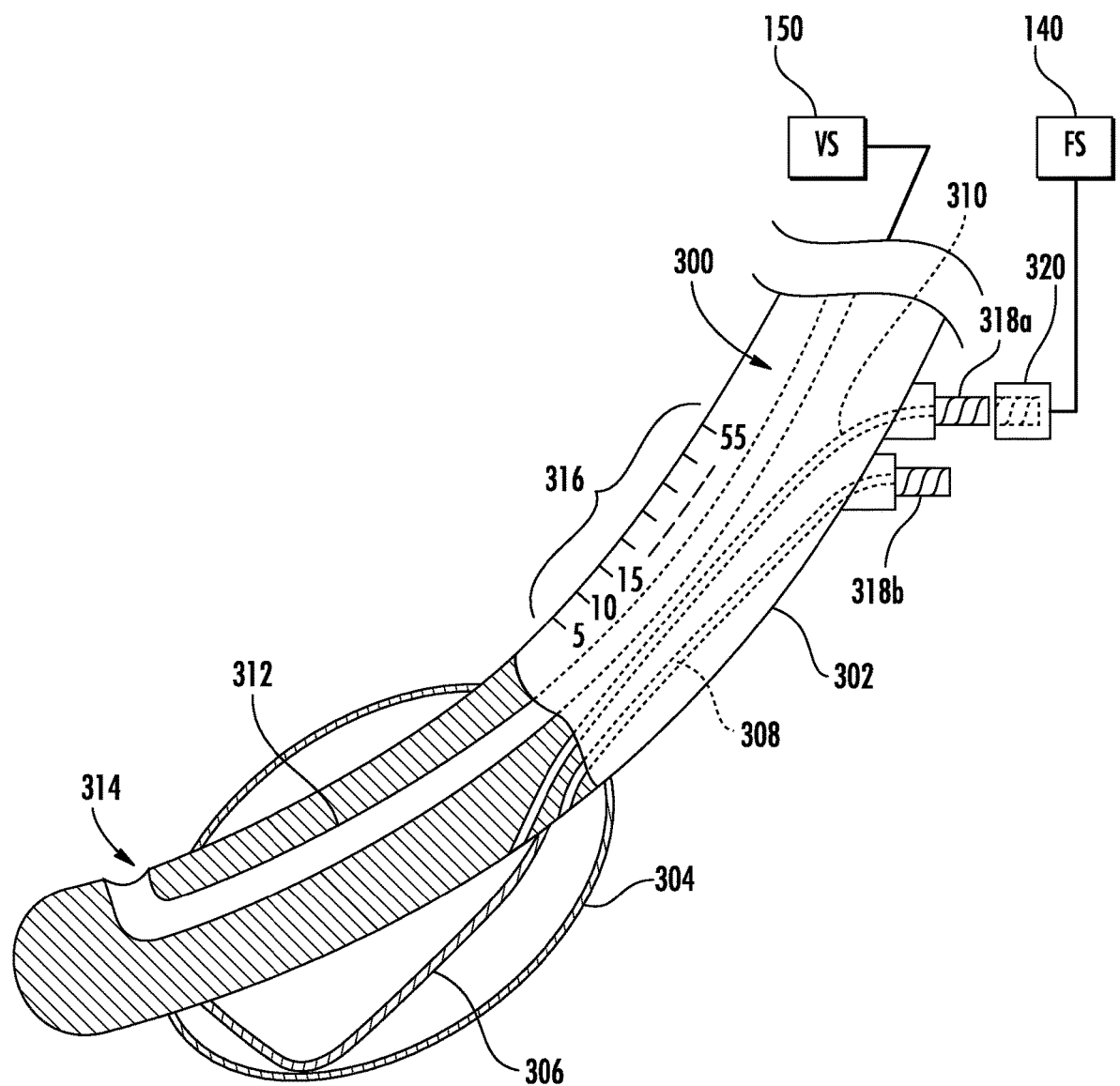
FIG. 11 is a side, partial cross-sectional view of a leading end portion of still another illustrative embodiment of a gastric calibration tube shown coupled to a fluid source and a vacuum source in accordance with the principles of the present disclosure.

Referring now to FIG. 11, another embodiment of a gastric calibration tube, generally referred to as gastric calibration tube 300, is shown. Gastric calibration tube 300 is substantially similar to gastric calibration tubes 100 and 200 and is only described herein to the extent necessary to describe the differences in construction and operation of the gastric calibration tube 300. In general, the gastric calibration tube 300 includes an elongate member 302 that supports a first balloon 304 and a second balloon 306 and operably couples to one or both of the fluid source 140 and the vacuum source 150. The second balloon 306 can function in a similar manner to the pushing member 130 of the gastric calibration tube 100.

The elongate member 302 defines a first lumen 308 in fluid communication with the first balloon 304 and a second lumen 310 in fluid communication with the second balloon 306. As shown in FIG. 11, the elongate member 302 defines an aspiration lumen 312 that is in fluid communication with a side opening 314 defined in an outer surface of the elongate member 302 at a distal end portion of the elongate member 302. In certain embodiments, the elongate member 302 includes one or more depth markings 316 on an outer surface of the elongate member 302 similar to the depth marking shown in FIG. 1B. A first connector 318a and a second connector 318b are secured to the outer surface of the elongate member 302. In certain embodiments, one or both of the first and second connectors 318a, 318b are luer connectors or any other suitable connector known in the art. The first connector 318a is in fluid communication with lumen 310 and the second connector 318b is in fluid communication with lumen 308. One or both of the fluid source 140 and the vacuum source 150 couple to one or both of the first and second connectors 318a, 318b by any suitable connection 320 coupled to the respective fluid and/or vacuum source 140, 150.

Figure 12:
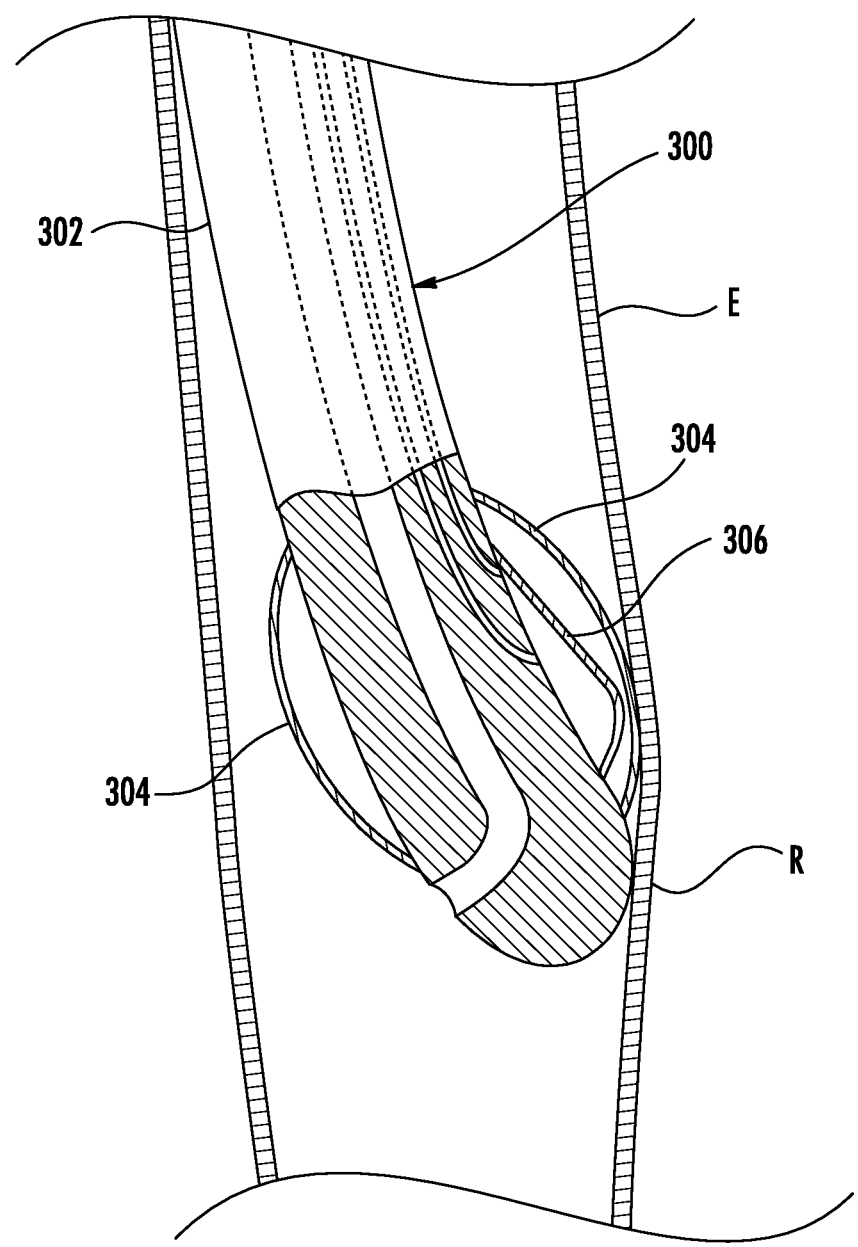
FIGS. 12-14 are progressive, side, partial cross-sectional views of the gastric calibration tube of FIG. 11 navigating through an esophagus.
Figure 13:
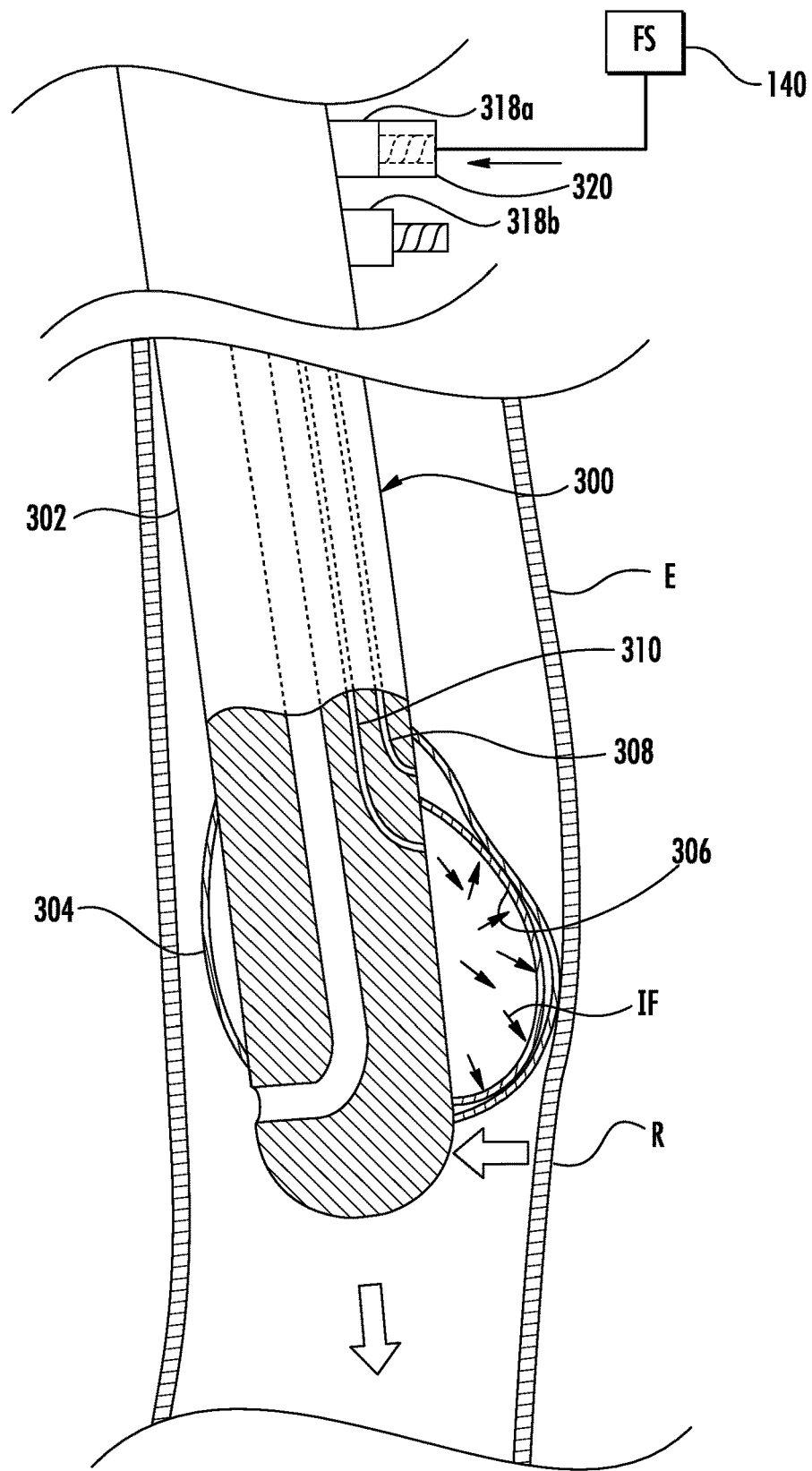
Figure 14:
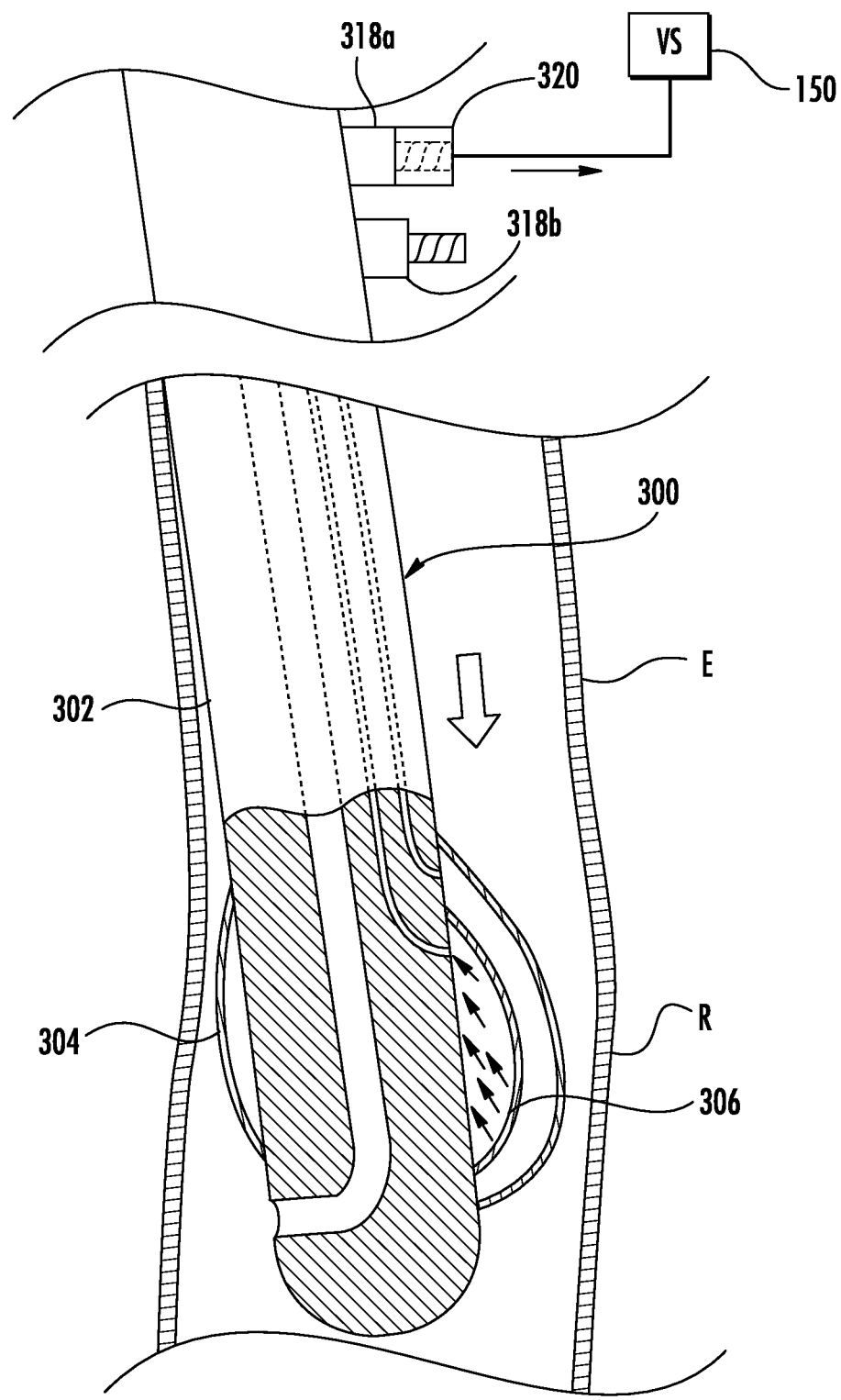

In use, with reference to FIGS. 12-14, the gastric calibration tube 300 is inserted into an oral cavity of a patient and advanced along the track through the esophagus "E" toward the patient's stomach "S." If the gastric calibration tube 300 encounters an obstruction or otherwise becomes misaligned while being advanced along the track, the second balloon 306 can be inflated (e.g., via the inflation fluid "IF" from the fluid source 140 such as saline).

During inflation, the second balloon 306 extends substantially laterally outwardly from the outer surface of the elongate member 302. The second balloon 306 is expandable to a dimension large enough to apply an expansion force to a surface of a structure along the track such as the inner surface of the esophagus "E." A reaction force responsive to the expansion force urges the elongate member 302 away from the obstruction/point of restriction "R," and/or otherwise realigns the elongate member 302 as desired.

The vacuum source 150 couples to the connector 318a so that the inflation fluid "IF" (e.g., saline) can be withdrawn from the second balloon 306 to deflate the second balloon 306 can be deflated to facilitate distal advancement of the elongate member 110.

Figures 15, 16:
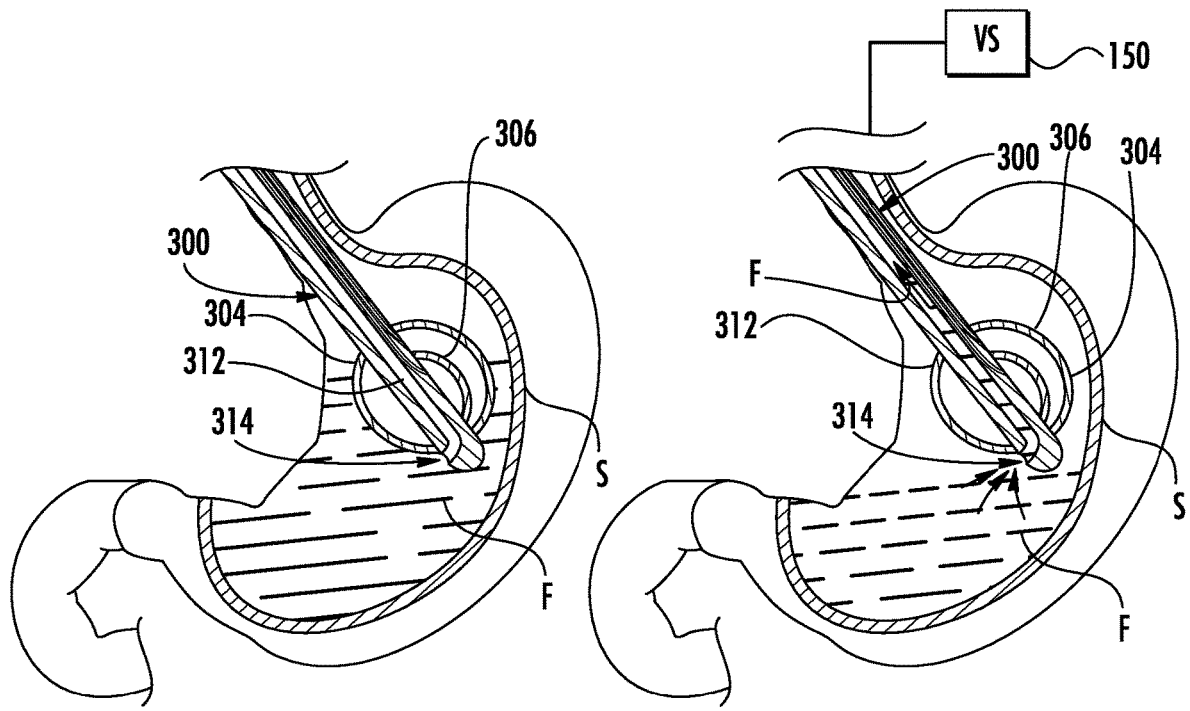
FIGS. 15-18 are progressive side views of the gastric calibration tube embodiment of FIG. 11, which illustrate aspirating bodily fluid from within a stomach and securement of the tube to the stomach.

Turning now to FIGS. 15-16, the vacuum source 150 can be positioned in fluid communication with the aspiration lumen 312 and used to aspirate bodily fluid "F" in the stomach "S" into the side opening 314 of the gastric calibration tube 300 for proximal extraction (see FIG. 16) therethrough as described above with regard to gastric calibration tube 100.

Figures 17, 18:
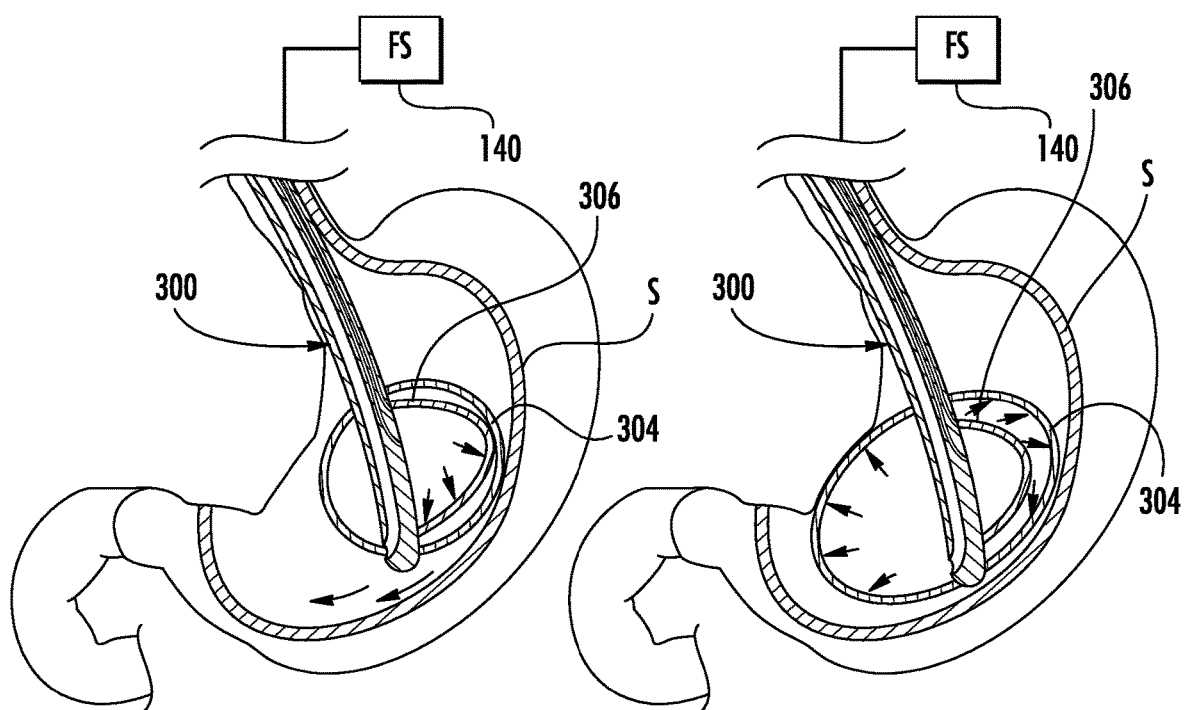

As shown in FIG. 17, the fluid source 140 couples to the connector 318a so that the second balloon 306 can be inflated into engagement with an inner surface of the stomach "S" to urge a leading end portion of the gastric calibration tube 300 toward any desirable location within the stomach "S" for inflating the first balloon 304 and/or for applying irrigation/aspiration within the stomach "S" (e.g., by virtue of the side opening 314). For example, reaction force resulting from engagement of the second balloon 306 with the inner surface of the stomach "S" positions the leading end portion of the gastric calibration tube 300 adjacent to the antrum of the stomach "S" so that the first balloon member 304 can be inflated within the antrum to fix the gastric calibration tube 300 within the stomach "S."

As shown in FIG. 18, the fluid source 140 couples to the connector 318b so that the first balloon 304 can be inflated to fix the gastric calibration tube 300 within the stomach "S" as described above with regard to the balloon 120 of the gastric calibration tube 100.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A gastric calibration tube, comprising:
a flexible elongate member defining a side opening and a lumen that is in communication with the side opening, the flexible elongate member having a distal end portion defining an aspiration lumen that extends distally to an opening defined in a distal end of the distal end portion;
a pushing member configured to advance through the lumen of the flexible elongate member and out of the side opening of the flexible elongate member; and
a balloon member secured to the pushing member and configured to maintain the gastric calibration tube within a patient's stomach.

2. A gastric calibration tube, comprising:
a flexible elongate member having a proximal end portion, a distal end portion, and an outer surface that extends between the proximal and distal end portions, the outer surface defining a side opening, the distal end portion defining an aspiration lumen that extends distally to an opening defined in a distal end of the distal end portion, the flexible elongate member including a launch curve and defining a lumen that are in communication with the side opening;
a pushing member having a proximal portion and a distal portion, the distal portion being advanceable through the lumen of the flexible elongate member so that the launch curve of the flexible elongate member can direct the distal portion of the pushing member out of the side opening of the flexible elongate member; and
a balloon member secured to at least one of the flexible elongate member and the pushing member, the balloon member being inflatable to fix the gastric calibration tube within a patient's stomach.

3. A method for advancing a gastric calibration tube, the method comprising:
advancing an elongate member through an oral cavity toward a stomach of a patient;
selectively advancing a pushing member through the elongate member and out of a side opening defined in an outer surface of the elongate member;
aspirating fluid within the stomach through an aspiration lumen defined in a distal end portion of the elongate member, the aspiration lumen extending distally to an opening defined in a distal end of the distal end portion; and
inflating a balloon supported on the pushing member in the stomach of the patient.

4. The method of claim 3, further including positioning the balloon within the antrum of the stomach.

5. The method of claim 3, further including orienting the side opening of the elongate member with a reference indicator supported on the elongate member.

6. The gastric calibration tube of claim 2, wherein the lumen is in fluid communication with at least one of a fluid source and a vacuum source.

7. The gastric calibration tube of claim 2, wherein the flexible elongate member includes at least one depth marking.

8. The gastric calibration tube of claim 2, wherein the flexible elongate member includes a reference indicator that identifies an orientation of the side opening.

9. The gastric calibration tube of claim 8, wherein the reference indicator is positioned proximally offset from the side opening.

10. The gastric calibration tube of claim 2, wherein the aspiration lumen extends through the launch curve to communicate with the lumen of the flexible elongate member through which the pushing member advances.

11. The gastric calibration tube of claim 1, wherein the aspiration lumen extends through a launch curve of the flexible elongate member to communicate with the lumen of the flexible elongate member through which the pushing member advances.

* * * * *